US00PP07920P

United States Patent [19]

Zaiger et al.

[11] Patent Number: Plant 7,920

[45] Date of Patent: Jul. 21, 1992

[54] NECTARINE TREE "ARCTIC SHOW"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of Modesto, Calif. 95351

[21] Appl. No.: 650,922

[22] Filed: Feb. 5, 1991

[51] Int. Cl.[5] ..... A01H 5/00

[52] U.S. Cl. ..... Plt./40.1

[58] Field of Search ..... Plt./40

*Primary Examiner*—James R. Feyrer

[57] ABSTRACT

A new and distinct variety of nectarine tree which has the unique combination of desirable features that are outstanding in a new variety:

1. Heavy and regular production of fruit.
2. Late maturing, white flesh, freestone nectarines.
3. Fruit with firm flesh, good handling and shipping qualities.
4. Vigorous upright growth.
5. Fruit with excellent flavor and eating quality.
6. The fruit staying firm on the tree 7 to 8 days after shipping ripe.

ORIGIN OF THE VARIETY

The present new variety of nectarine tree was originated by us in our experimental orchard located near Modesto, Calif., as a first generation cross between two selected seedlings with the field identification numbers 35EB252 and 35GC20. The female parent with the identification number 35EB252 originated from a second generation cross between two selected seedlings. One with the parentage of Sun Grand Nectarine (U.S. Plant Pat. No. 974) crossed with Merril Gem Peach (U.S. Plant Pat. No. 868) and the other seedling was selected from a second generation cross between a late maturing nectarine of unknown parentage crossed with Autumn Grand Nectarine (Plant Patent No. 2894). The pollen parent with the identification number 35GC20 originated as a second generation seedling from a cross between Redwing Peach (Plant Patent No. 621) and a very firm, high colored nectarine of unknown parentage. A large group of these first generation seedlings was planted and grown under careful observation by us. One such seedling, which is the present variety, having especially desirable late maturing fruit was selected for asexual reproduction and commercialization.

1 Drawing Sheet

ASEXUAL REPRODUCTION OF THE VARIETY

The present new variety of nectarine tree was asexually reproduced by budding, as performed by us in our experimental orchard located near Modesto, Calif., and shows that all characteristics come true to the original tree and are established and transmitted through succeeding propagations.

SUMMARY OF THE VARIETY

The new and distinct variety of nectarine tree is of large size, vigorous upright growth, a regular and productive bearer of large size, white flesh, freestone fruit with excellent flavor and eating quality. The fruit is further characterized by being of firm flesh with good handling and shipping qualities, having the ability to stay firm on the tree 7 to 8 days after maturity (shipping ripe) and maturing in the late season approximately 10 days after Autumn Grand Nectarine (U.S. Plant Pat. No. 2,894).

DESCRIPTION OF THE PHOTOGRAPHS

The accompanying color photographs show typical specimens of the fruit and foliage of our new variety. A small branch with the upper and lower surface of the leaves are illustrated, as well as specimens of the fruit with the exterior and a sectional view showing flesh coloration, pit cavity and a stone remaining in place. The photographs were taken shortly after the fuit was picked at maturity (shipping ripe) and the colors are as nearly true as is reasonably possible in a color representation of this type.

DESCRIPTION OF THE VARIETY

The detailed botanical description of our new and distinct variety of nectarine tree, its flowers, fruit and foliage, is based on observations of specimens grown near Modesto, Calif., with color terminology (except those in common terms) in referenced to Reinhold Color Atlas by A. Kornerup and J. H. Wanscher.

Tree:
- *Size.*—Large.
- *Vigor.*—Vigorous.
- *Growth.*—Upright.
- *Density.*—Medium dense.
- *Production.*—Productive.
- *Bearing.*—Regular.
- *Shape.*—Usually pruned to vase shape.

Trunk:
- *Size.*—Medium stocky.
- *Surface.*—Medium shaggy.
- *Color.*—Brown to grayish brown (6-E-6) to (6-F-6).

Branches:
- *Size.*—Medium.
- *Texture.*—Smooth to medium rough.
- *Lenticels.*—Numerous. Medium Size.
- *Color.*—Reddish brown to brown (8-E-5) to (8-E-7).

Leaves:
- *Size.*—Large. Average length — 6". Average width — 1½".
- *Form.*—Lanceolate. Pointed.
- *Thickness.*—Medium.

*Margin.*—Crenate.
*Petiole.*—Medium length. Medium thickness.
*Texture.*—Smooth.
*Glands.*—Primarily Globose, some Reniform. Number varies from 0 to 4. Average number 2. Medium size. Located on the lower portion of the leaf blade and upper portion of petiole.
*Color.*—Upper surface — green to dark green (2-F-5) to (28-F-7). Lower surface — Lower surface — green to grayish green (28-E-6) to (28-E-8).

Flower Buds:
*Size.*—Medium to large.
*Form.*—Plump.
*Length.*—Medium.

Flowers:
*Blooming period.*—Mar. 3, 1990 to Mar. 9, 1990. Varies slightly due to climatic variations.
*Size.*—Large — showy.
*Pollen.*—Present.
*Color.*—Pink.

Fruit:
*Maturity when described.*—Firm ripe.
*Date of first picking.*—Sept. 1, 1990.
*Date of last picking.*—Sept. 6, 1990.
*Size.*—Large. Average diameter axially — 2¾" to 3". Average transversely in suture plane — 2⅞ to 2 15/16".
*Form.*—Globose, nearly symmetrical, some fruit slightly larger in suture plane.
*Suture.*—Shallow — extends from base to apex.
*Ventral surface.*—Nearly round, only very slightly lipped.
*Apex.*—Varies from round to very slight pistil point.
*Base.*—Retuse.
*Cavity.*—Rounded, slightly elongated in suture plane. Depth — ½". Breadth — ⅞".

Skin:
*Thickness.*—Medium.
*Texture.*—Medium, tenacious to the flesh.
*Tendency to crack.*—None.
*Down.*—Wanting.
*Color.*—White to pinkish white ground color (10-A-1) to (10-A-2). Overspread with a high percentage of red to turkish red (10-B-7) to (10-C-8).

Flesh:
*Ripens.*—Evenly.
*Texture.*—Firm.

*Juice.*—Moderate.
*Aroma.*—Slight.
*Fibers.*—Few, small, tender.
*Flavor.*—Excellent, mild, sub-acid, sweet.
*Eating quality.*—Excellent.
*Color.*—White (11-A-1). Pit cavity red to geranium red (11-A-7) to (11-B-8) with slight bleeding of red (11-A-7) into flesh surrounding pit cavity.

Stone:
*Type.*—Freestone.
*Size.*—Large. Average length — 1½". Average width — 1". Average thickness — ⅞".
*Form.*—Oval to slightly obovate.
*Base.*—Varies from round to straight.
*Apex.*—Cuspidate.
*Surface.*—Irregularly furrowed toward apex, pitted toward base. Pit cavities vary from elongated to round.
*Ridges.*—Varies from smooth to rough.
*Sides.*—Nearly equal.
*Tendency to split.*—None.
*Color.*—Varies from dark brown to reddish brown (9-E-7) to (9-F-7).

Use: Dessert.
*Markets.*—local and long distance.
Keeping quality: Good
Shipping quality: Good.

The present variety of nectarine tree, its flowers and fruit herein described may vary in slight detail due to climatic, soil types and cultural practices under which the variety may be grown. The present botanical description is that of the variety grown under the ecological conditions prevailing near Modesto, Calif.

We claim:

1. A new and distinct variety of nectarine tree, substantially as illustrated and described, characterized by its large size, vigorous upright growth, and a productive and regular bearer of large, firm, white flesh, freestone fruit with good storage and shipping qualities; the fruit is further characterized by its excellent flavor and eating quality and its late ripening, maturing approximately 10 days after Autumn Grand Nectarine (U.S. Plant Pat. No. 2,894).

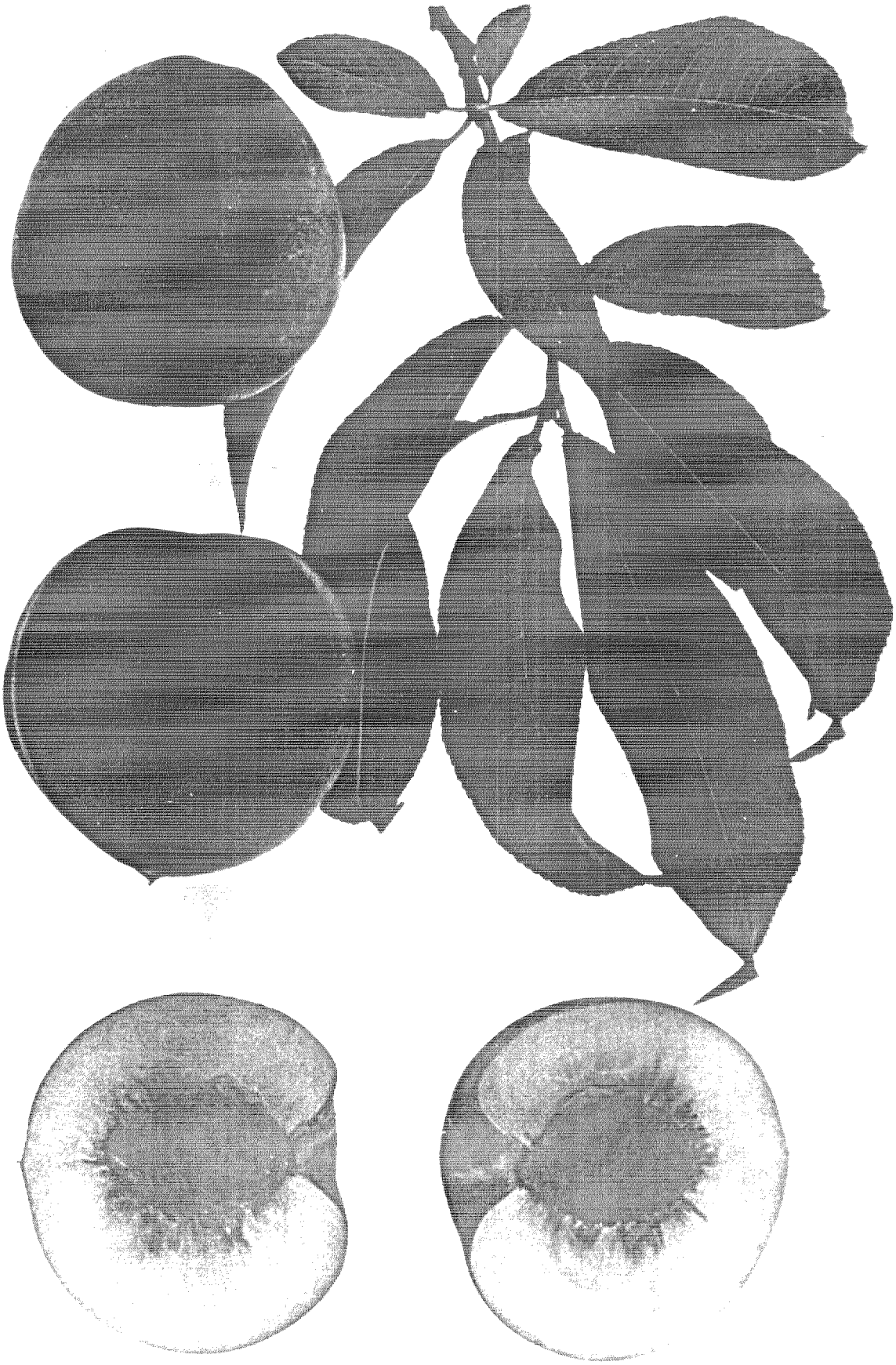

* * * * *